(12) United States Patent
DeShazer

(10) Patent No.: US 10,159,594 B2
(45) Date of Patent: Dec. 25, 2018

(54) FOLEY CATHETER BAG SUPPORT SLEEVES

(71) Applicant: Kenna DeShazer, Sweet Home, OR (US)

(72) Inventor: Kenna DeShazer, Sweet Home, OR (US)

(*) Notice: Subject to any disclaimer, the term of this patent is extended or adjusted under 35 U.S.C. 154(b) by 463 days.

(21) Appl. No.: 14/933,857

(22) Filed: Nov. 5, 2015

(65) Prior Publication Data

US 2017/0128255 A1    May 11, 2017

(51) Int. Cl.
*A61F 5/44* (2006.01)
*A61F 5/451* (2006.01)

(52) U.S. Cl.
CPC .......... *A61F 5/4408* (2013.01); *A61F 5/4405* (2013.01); *A61F 5/451* (2013.01)

(58) Field of Classification Search
CPC .......... A61F 5/44; A61F 5/4408; A61F 5/451
See application file for complete search history.

(56) References Cited

U.S. PATENT DOCUMENTS

| | | | |
|---|---|---|---|
| 5,032,118 A | 7/1991 | Mason | |
| 5,643,236 A * | 7/1997 | Hadley | A61F 5/4408 128/DIG. 15 |
| 5,935,116 A | 8/1999 | Kristensen | |
| 6,887,223 B2 | 5/2005 | Bisbee | |
| 7,077,833 B2 | 7/2006 | Bonham | |
| 2011/0224636 A1* | 9/2011 | Keisic | A61F 5/44 604/328 |
| 2014/0207093 A1* | 7/2014 | Marshall | A61F 5/44 604/327 |

* cited by examiner

*Primary Examiner* — Jacqueline Stephens
*Assistant Examiner* — Kai Weng
(74) *Attorney, Agent, or Firm* — Mohr Intellectual Property Law Solutions, PC (57) ABSTRACT

Foley catheter bag support sleeves for receiving and securing a catheter bag that can be secured to the inside of a user's clothes, including flexible support sleeves preferably made with fabric that are equipped with a lining on at least one side to avoid irritation to the user's skin. In some examples, the catheter bag support sleeve is secured using hook or loop material (such as Velcro®) that mates with corresponding material that is attached to the interior of a garment worn by the user, such as a pair of pants. In other examples, the catheter bag support sleeve can be secured to the user's garment using any removable attachment means. In some further examples, the support sleeve includes ends that can be opened or secured shut to provide alternative or additional securing of an enclosed catheter bag.

16 Claims, 8 Drawing Sheets

FOLEY CATHETER BAG SUPPORT SLEEVES

BACKGROUND

The present disclosure relates generally to medical appliances for patients that require the use of a foley catheter bag. In particular, support sleeves for securely holding catheter bags that can be comfortably worn underneath a user's clothing are described.

Patients that suffer from urinary incontinence or, for any number of medical reasons are unable to relieve their bladders conventionally, may need to resort to a medical device known as a foley catheter bag. The device uses a tube that discharges into the catheter bag for collection. The user wears the catheter bag continuously while going about the user's daily routine.

Figure 1:
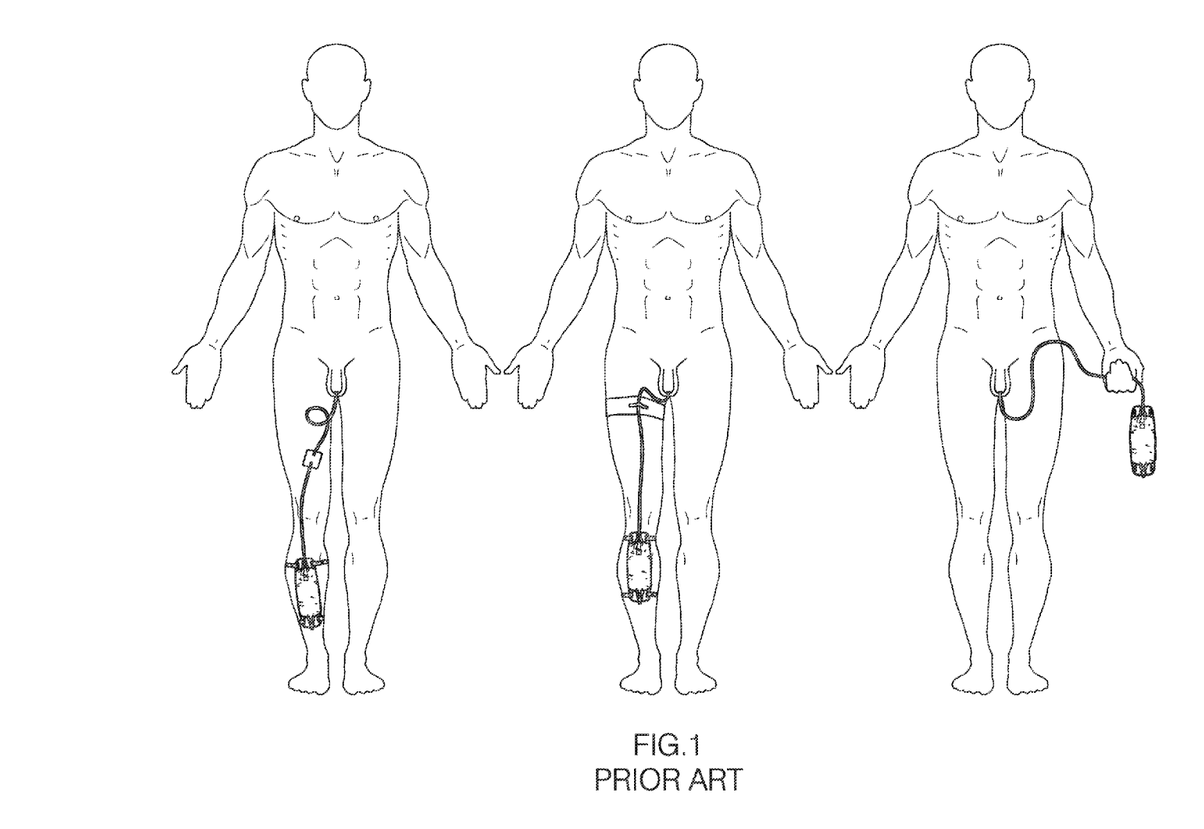
FIG. 1 is a series of diagrams that depict several ways in which catheter bags are worn by users as known in the prior art.
Figure 2:
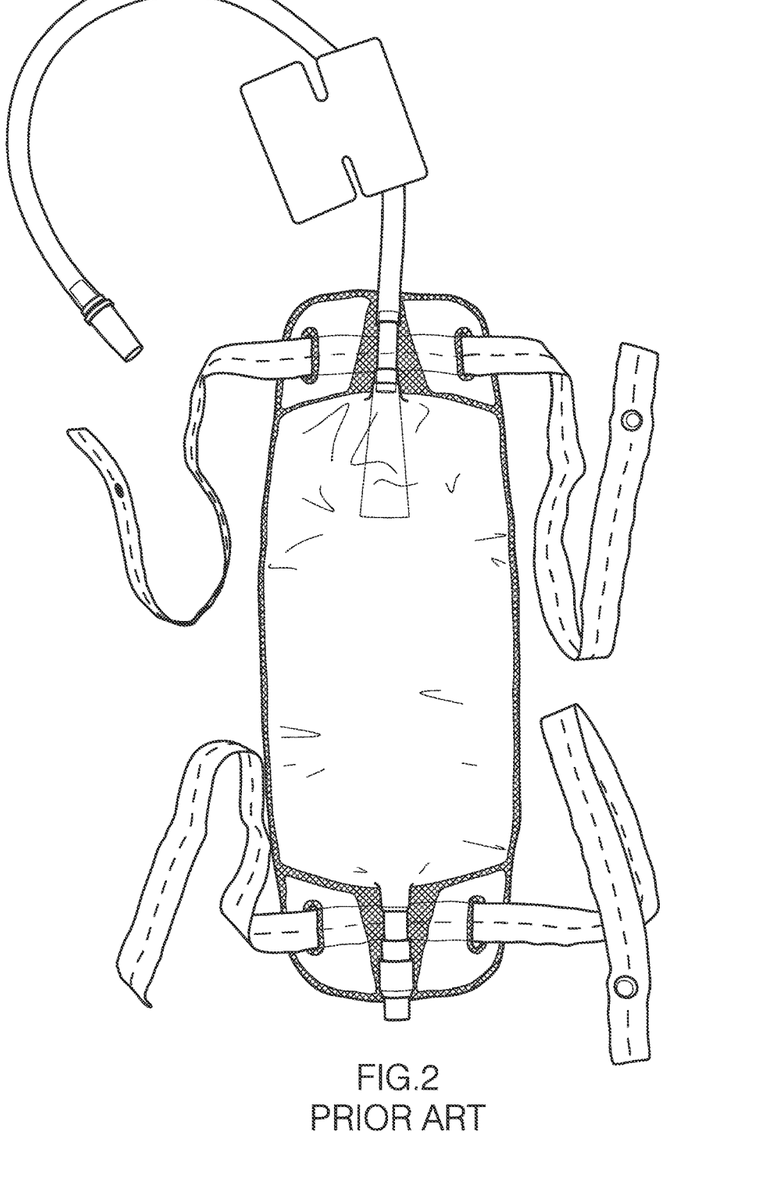
FIG. 2 is a perspective view of a catheter bag and associated straps and tube support for wearing a catheter bag as presently done in the prior art.

Known approaches and equipment for wearing foley catheter bags are not entirely satisfactory for the range of applications in which they are employed. For example, as can be seen in FIG. 1, prior art methods of wearing a catheter bag typically involve strapping the bag to some portion of the user's leg under the user's clothes, or carrying the bag externally, which discloses its existence. The discharge tube is typically secured to the user at some intermediate point between the bag and the catheter to isolate the catheter from unwanted (and potentially painful) movement. FIG. 2 shows a close-up view of the catheter bag with the prior art straps for securing the bat directly to a user's leg, as well as an adhesive strip for securing the tube and isolating the catheter from movement.

These means of attaching and wearing a catheter Dag are not entirely reliable. Strapping a bag to a user's leg carries with it a substantial risk that the catheter bag could inadvertently slip down and be exposed, causing both embarrassment and, if the tube is not sufficiently secured, pain from a moving catheter. The straps are limited in how tightly they may be cinched to avoid interfering with the user's circulation. Consequently, a user must take care in day day activities to avoid inadvertently dislodging the bag. Furthermore, the catheter bag, by definition being made of a waterproof material, traps sweat and may irritate some user's skin when worn in direct contact, along with repeated use of an adhesive strip for securing the relief tube. Finally, inadvertent slipping of the catheter bag and/or failure of an adhesive strip to sufficiently hold the relief tube in place can increase the likelihood of the user developing a urinary tract infection.

Thus, there exists a need for devices for wearing catheter bags that improve upon and advance the design of known devices for wearing catheter bags. Examples of new and useful catheter bag support sleeves relevant to the needs existing in the field are discussed below.

Disclosure addressing one or more of the identified existing needs is provided in the existing detailed description below. Examples of references relevant to the disclosed catheter bag support sleeves include U.S. Pat. Nos. 5,032,118, 5,935,116, 6,887,223, and 7,077,833. The complete disclosures of the above patents and patent applications are herein incorporated by reference for all purposes. These references disclose alternatives to using straps to secure catheter bags to a user; however, most require the user to wear some additional undergarment.

SUMMARY

The present disclosure is directed to foley catheter bag support sleeves that receive and secure a catheter bag, and in turn can eke secured to the inside of a user's clothes. The support sleeve is flexible and preferably made with fabric, and can be equipped with a lining on at east one side to avoid irritation to the user's skin. The catheter bag can be secured within the support sleeve, which is substantially tubular, using buttons or another type of removable attachment means. The support sleeve may be equipped with at least one cutout that allows the enclosed catheter bag to be drained without removal from the sleeve. In some examples, the catheter bag support sleeve is secured using hook or loop material (such as Velcro®) that mates with corresponding material that is attached to the interior of a garment worn by the user, such as a pair of pants. In other examples, the catheter bag support sleeve can be secured to the user's garment using any removable attachment means. In some further examples, the support sleeve includes ends that can be opened or secured shut to provide alternative or additional securing of an enclosed catheter bag.

DETAILED DESCRIPTION

The disclosed foley catheter bag support sleeves will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation s not individually described in the following detailed description.

Throughout the following detailed description, examples of various foley catheter bag support sleeves are provided.

Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

With reference to FIGS. 3A-6 first example of a catheter bag support sleeve, sleeve 100, will now be described. Sleeve 100 functions to provide a pouch that surrounds a catheter bag and secures it into place in a comfortable fashion for the user, while not impeding its functionality or in any way requiring the user to limit his or her daily activities. The reader will appreciate from the figures and description below that sleeve 100 addresses shortcomings of conventional catheter bag apparatuses and methods.

For example, by securing the catheter bag within a pouch that is preferable made of a fabric that is non-irritating to skin, sleeve 100 makes wearing the catheter bag for extended periods of time more comfortable, alleviating the irritation and trapping of sweat that can be induced when a catheter bag is in direct contact with a user's skin. Sleeve 100 also is preferably secured to the interior of a user's garment using a means not subject to easy slippage, thereby eliminating a user's concerns that the catheter bag my become inadvertently exposed in public. By eliminating the possibility of accidental slippage, the user is also freed from the need to potentially limit daily activities, previously needed to avoid accidental slippage. Further, by reliably securing the catheter bag, the need to employ adhesive strips to immobilize the collection tube can be eliminated. Where sleeve 100 is secured to the user's garments relatively close to the crotch region, the movement of the collection tube is relatively minimal, reducing, if not altogether eliminating, any associated pain and the increased risk of urinary tract infections.

Turning particularly to FIGS. 3A-3D, catheter bag support sleeve 100 includes a pouch 102 sized to receive a catheter bag 104 and allow for its normal operation. Pouch 102 is comprised of a flexible material, and further incorporates one or more bag attachment points 106 for securing catheter bag 104 within pouch 102. Pouch 102 can be equipped with one or more openings 108 on a front side of the bag to allow catheter bag 104 to be drained without removal from pouch 102, and one or more pouch attachment points 110 on a top end of the pouch for removably securing pouch 102 to an article of clothing 112 worn by a user 114.

Figure 3A:
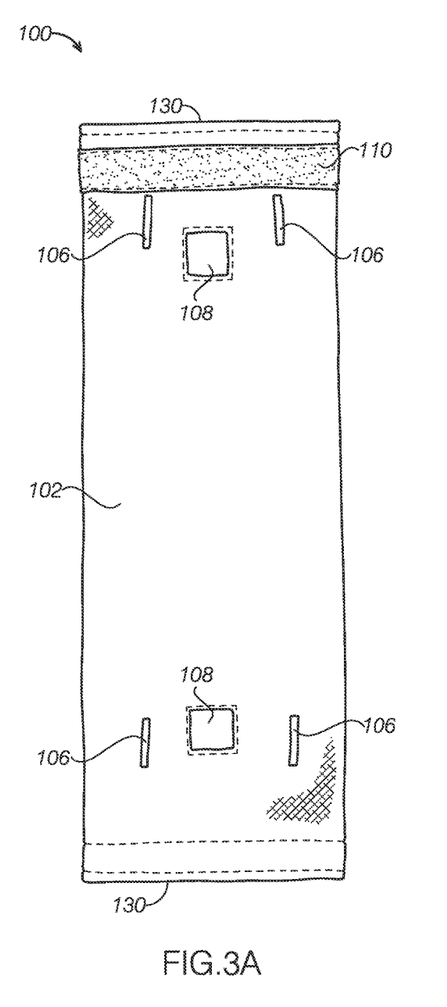
FIG. 3A is a front view of a first example of a catheter bag support sleeve.

As depicted in FIG. 3A, pouch 102 is essentially a flattened tube, constructed out of flexible material and sized to receive a catheter bag 104 of dimensions typical to the type of catheter bag 104 that user 114 normally uses. Pouch 102 must be sized so as to not interfere with the normal operation of catheter bag 104 as it receives urine. Pouch 102 is preferably constructed out of a material that is lightweight and breathable and will resist trapping sweat and heat, so as to improve user comfort while wearing. The material also should be suitably durable so as to withstand the frictions of being held between article of clothing 112 and user's 114 body, as well as preferably be machine washable. Examples of such materials include natural or synthetic fabrics such as cotton, silk, polyester, nylon, rayon, or a blend of natural and synthetic fibers, or any other material now known or later developed that offers durability, washability, breathability, and is non-irritating. Pouch 102 can optionally be printed with patterns or prints if user 114 desires a degree of customization or individualization.

Figure 3B:
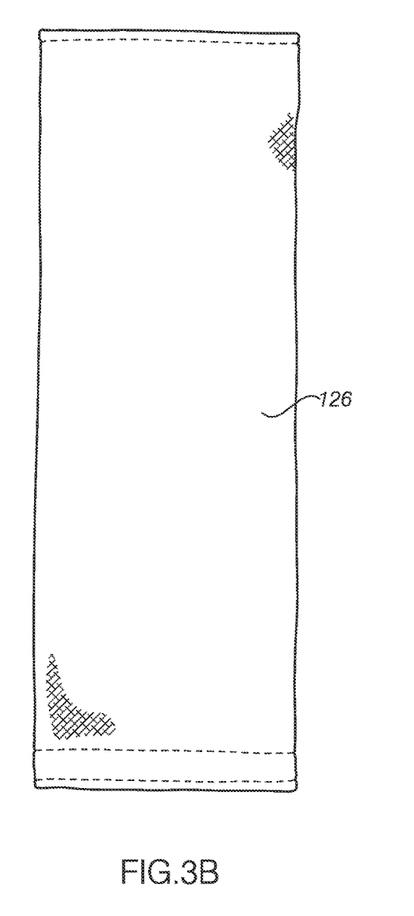
FIG. 3B is a back view of the catheter bag support sleeve shown in FIG. 3A depicting the portion of the sleeve that is lined with a non-irritating material for direct contact with a user's skin.

The back side of pouch 102, depicted in FIG. 3B, may optionally be covered by a layer of material 126 that is designed specifically to minimize irritation when in direct contact with user's 114 skin. Layer of material 126 may be constructed from natural or synthetic materials, including materials such as flannel, velvet, microfiber, or any other suitable non-irritating material now known or subsequently developed. Where pouch 102 is equipped with layer of material 126, pouch 102 may be constructed of material where non-irritation is less of a consideration. Pouch 102 may also be constructed such that layer of material 126 is integral to the construction, viz, the side of pouch 102 that faces article of clothing 112 is constructed of one type of durable and flexible material, while the side of pouch 102 that faces the user is constructed from the above-discussed material designed to minimize irritation to the user's skin. It will be understood that where pouch 102 is so constructed, layer of material 126 is an integral part of pouch 102, as opposed to a covering layer. A person skilled in the relevant art will appreciate that when layer of material 126 is an integral part of the construction of pouch 102, the material chosen for layer of material 126 should have a degree of structural durability that might not otherwise be required when layer of material 126 is a covering over pouch 102.

Figure 3C:
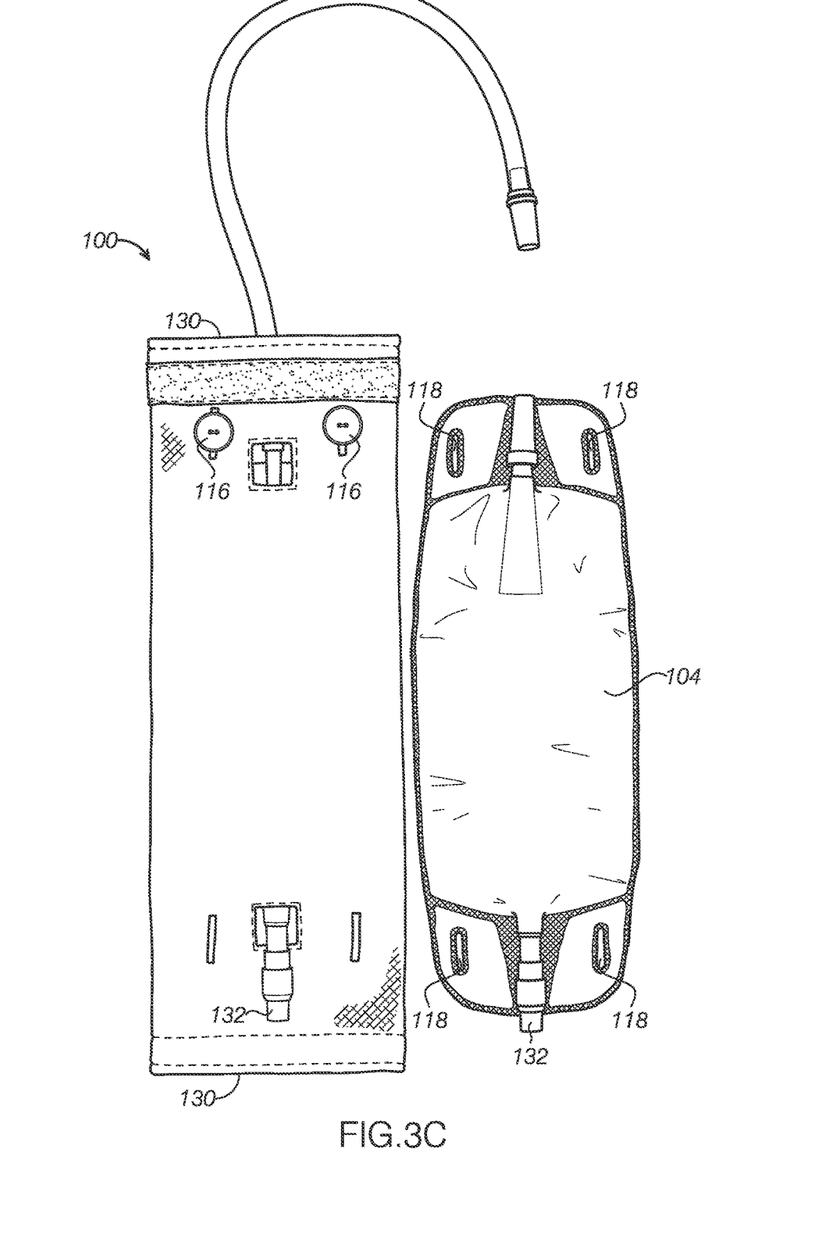
FIG. 3C is a front view of the catheter bag support sleeve shown in FIG. 3A depicting a catheter bag in perspective with the catheter bag support sleeve.

Catheter bag 104, depicted in FIG. 3C next to pouch 102, is typically equipped with one or more receiving slits 118. As can be seen in FIG. 2, these receiving slits 118 are used in the prior art to secure catheter bag 104 with a series of elastic straps. In sleeve 100, receiving slits 118 can be used to secure catheter bag 104 into pouch 102 by aligning them with bag attachment points 106. In the example depicted in FIG. 3C, bag attachment points 106 are equipped with buttons 116, which are each sized so as to fit through receiving slits 118 to effectively secure catheter bag 104 within pouch 102. Catheter bag 104 typically is equipped with orifices on each end for the introduction and drainage of urine. A relief tube running from a catheter typically attaches to one orifice, while a drain valve 132 attaches to the orifice on the opposite end.

Pouch 102 may be equipped with one or more openings 108 on a front side of the bag through which the drain valve can be actuated for convenient emptying of catheter bag 104 without necessitating removal from pouch 102. As can be seen in FIG. 3A, such openings 108 can also be placed near the opening of pouch 102 that is proximate to the relief tube of catheter bag 104, which can be used to run the relief tube if the configuration of catheter bag 104 allows, and if so desired by user 114, where the opening 108 suspends the drain valve of the catheter bag 104 above the recloseable ends 130 on the bottom of pouch 102.

Also seen in FIG. 3C are recloseable ends 130 of pouch 102, which are equipped with a recloseable material such as hook and loop, a zipper, groove and channel, or any other type of mechanism for selectively opening or sealing shut the ends of pouch 102. These recloseable ends 130 allow for catheter bag 104 to be inserted into pouch 102, and can then be closed to seal catheter bag 104 inside pouch 102. Thus, recloseable ends 130 add a redundant method of securement to catheter bag 104 in the event that catheter bag 104 is not correctly secured to bag attachment points 106, such as if receiving slits 118 are torn, or if a different model of catheter bag 104 is used that lacks the ability to be secured via bag attachment points 106.

Figure 3D:
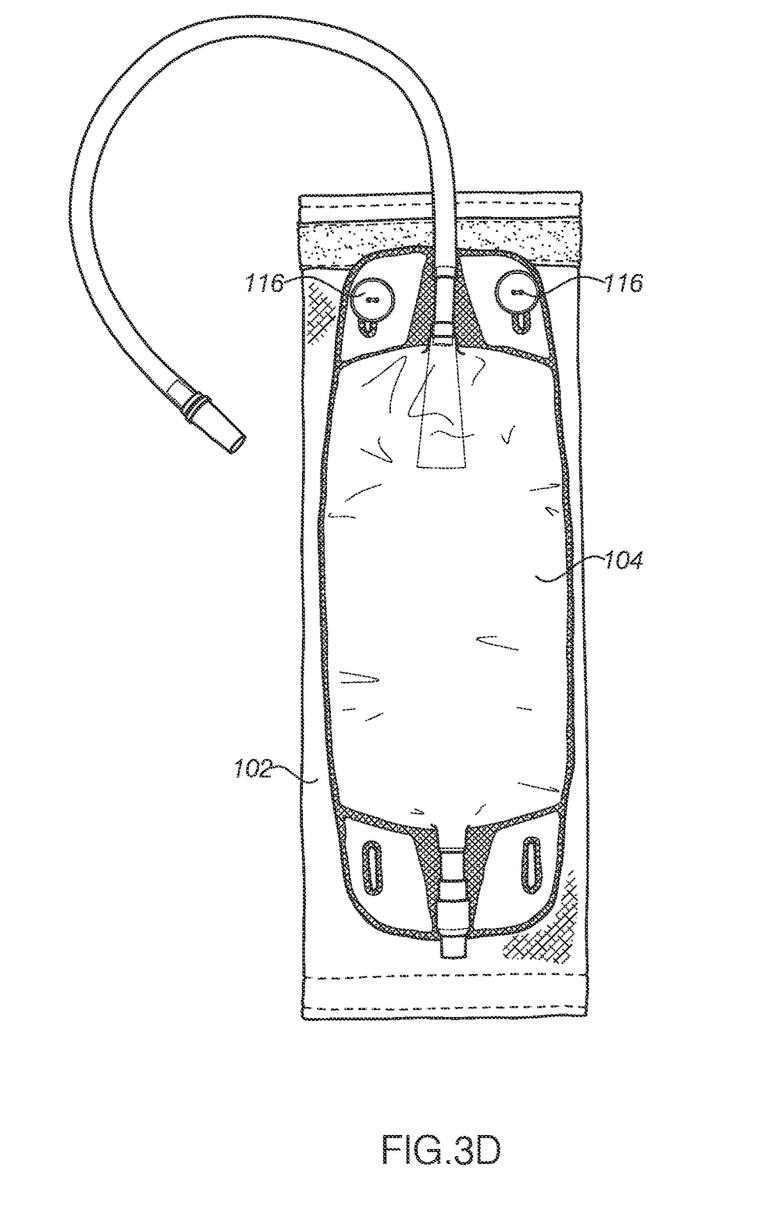
FIG. 3D is a front transparent view of the catheter bag support sleeve shown in FIG. 3A depicting the catheter bag as inserted and secured into the catheter bag support sleeve.

FIG. 3D depicts catheter bag 104 as it can be secured within pouch 102. Attachment points 106 are equipped with buttons 116, which have been passed through receiving slits 118, thereby securely yet removably affixing catheter bag 104 within pouch 102. It will be appreciated by a person skilled in the relevant art that while buttons 116 are presented as one means for securing catheter bag 104 within pouch 102, they are not the only means. Attachment points 106 could be equipped with alternative means for securing catheter bag 104 within pouch 102 such as hook or loop material (with corresponding loop or hook material on catheter bag 104), clamps, safety pins, cords, button snaps with either the mating halves affixed to catheter bag 104 or alternatively attached to the side of pouch 102 opposing attachment points 106 so that the two mating halves pass through each receiving slit 118, hooks, ties, adhesive patches, or any other fastening mechanism or device that allows catheter bag 104 to be removably secured within pouch 102.

Figure 4:
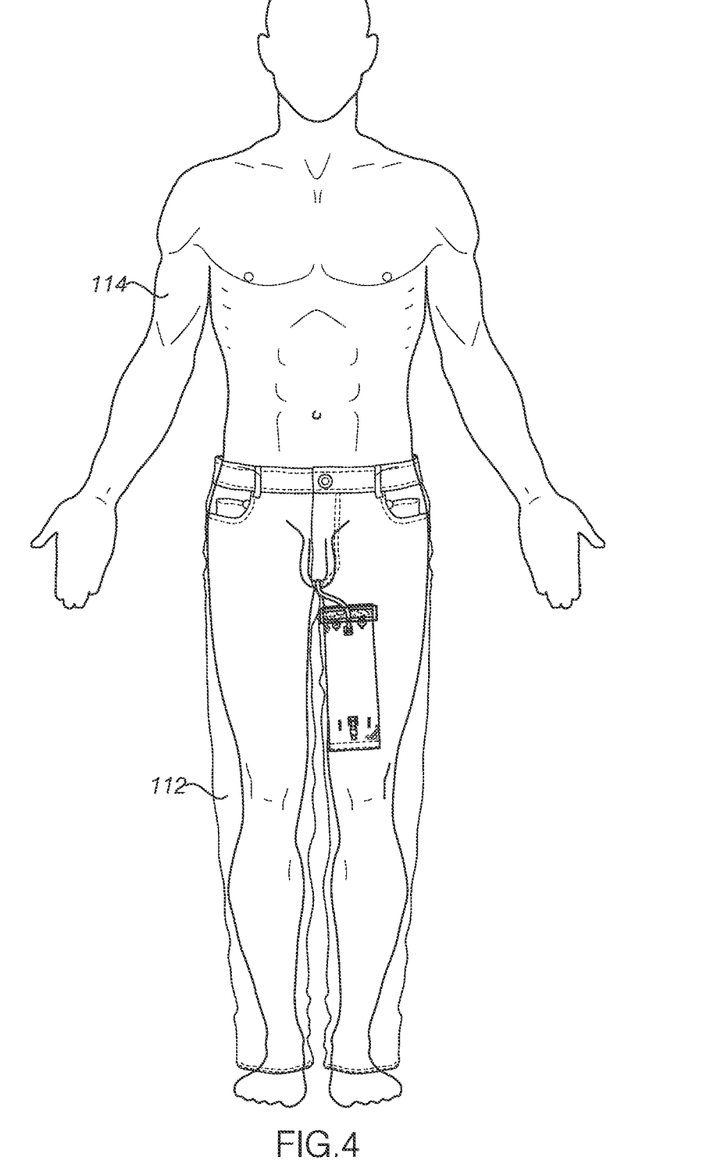
FIG. 4 is a diagrammatic view of the catheter bag support sleeve shown in FIG. 3A depicting its usage by a user.

In FIG. 4, the manner in which catheter bag support sleeve 100 is used on user 114 is depicted. Pouch 102, with catheter bag 104 affixed inside, is in turn affixed on the inside of article of clothing 112 exclusively by the pouch attachment points 110 with the top end vertically elevated above the bottom end of the pouch 102. As catheter bag 104 is held relatively immobile inside pouch 102 which is in turn held relatively immobile inside of article of clothing 112, user 114 can go about daily activities without limitation and without worry that catheter bag 104 will be exposed or be subject to movement that could cause user 114 pain. Moreover, notably lacking in FIG. 4 is an adhesive strip to secure the relief tube to user's 114 leg. Instead, the pouch 102, with the catheter bag 104 affixed inside, hangs freely from the article of clothing exclusively by the pouch attachment point, and is not secured to a user's 114 leg.

Figure 5:
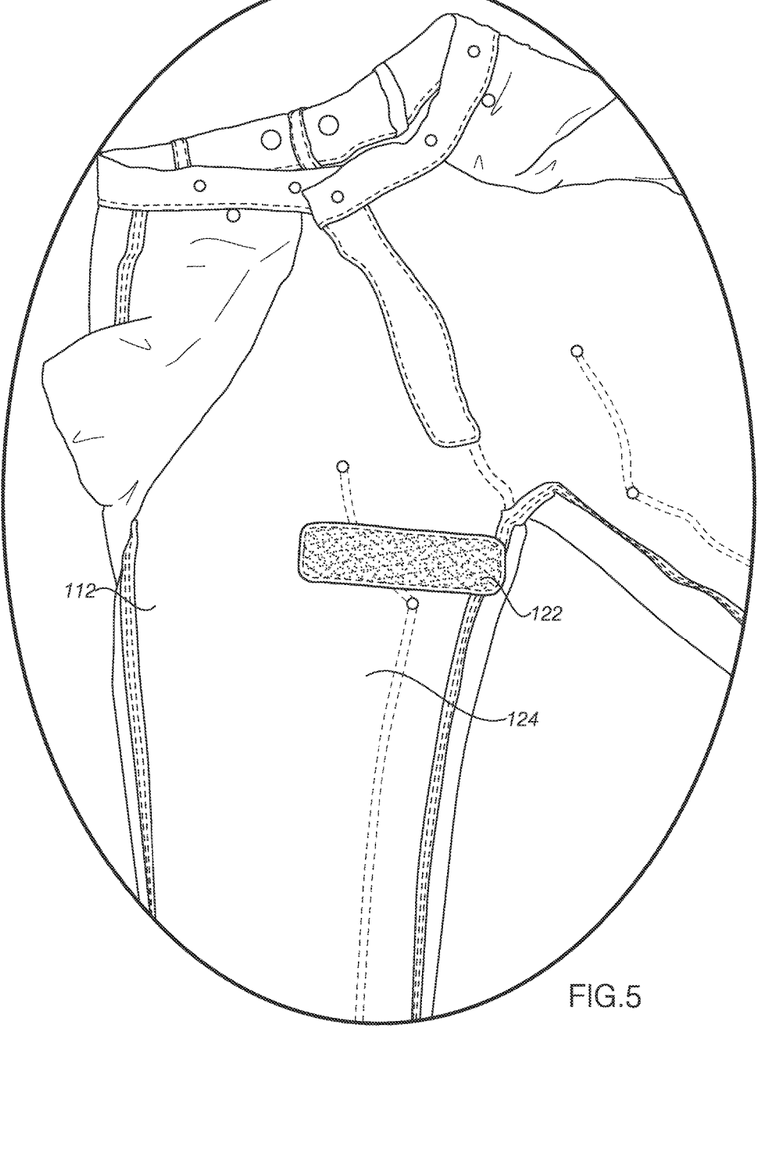
FIG. 5 is a perspective view of a pair of jeans that may be worn by a user of the catheter bag support sleeve shown in FIG. 3A, depicting the interior surface of the jeans and associated mounting point for the catheter bag support sleeve.

In FIG. 5, the means by which pouch 102 is removably secured to article of clothing 112 is demonstrated. Pouch 102 is fitted with one or more areas of hook or loop material on pouch attachment point 110. A corresponding area of loop or hook material 122 is affixed to the inner surface 124 of article of clothing 112, depicted in FIG. 5 as inside-out. The loop or hook material 122 can be secured to article of clothing 112 in any suitable fashion that allows it to remain affixed even while bearing the weight of a partially full or full catheter bag 104 within pouch 102, such as sewing, adhesives such as iron-heat activated or hot glue, or any other suitable fashion now known or later developed. Loop or hook material 122 could optionally be made part of or implemented as a part of inner surface 124, such as where inner surface 124 is lined with a fabric to which hook or loop material on pouch attachment point 110 will adhere. While FIG. 5 only depicts one area of loop or hook material 122, multiple such areas could be employed, which could correspond to one or more pouch attachment points 110. Moreover, multiple areas of hook or loop material 122 could be installed in an article of clothing 112, allowing user 114 to select the leg on which he or she wishes to attach sleeve 100.

It will be appreciated by a person skilled in the relevant art that hook and loop material is only one possible means for securing pouch 102 to article of clothing 112. Other such means could include safety pins, button snaps, buttons, hooks, cords, pockets, zippers, or any other device or method for fastening pouch to article of clothing 112 in a removably secure fashion that can hold the weight of pouch 102 with a full catheter bag 104.

Figure 6:
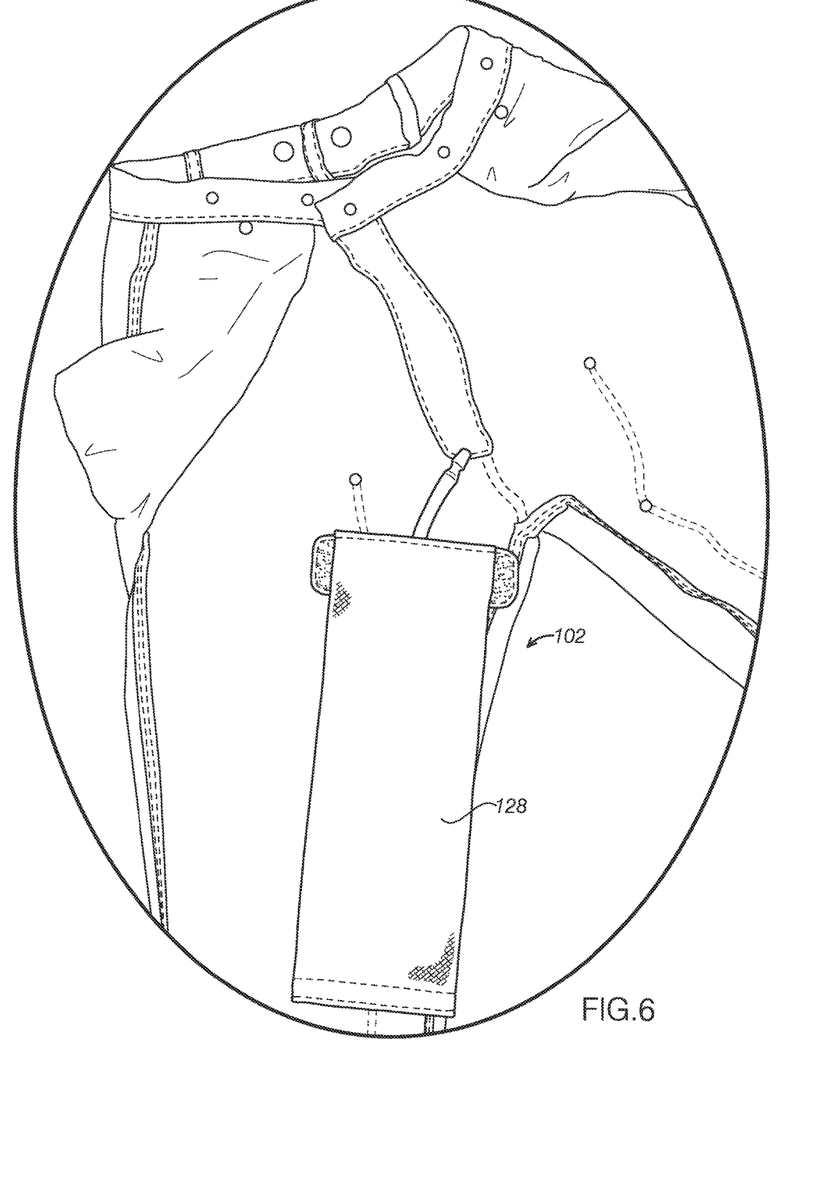
FIG. 6 is a perspective view of the catheter bag support sleeve shown in FIG. 3A depicting the catheter bag mounted and attached to the interior surface of a pair of jeans that may be worn by the user.

Turning to FIG. 6, catheter bag support sleeve 100 is depicted installed on inner surface 124 of article of clothing 112. The hook and loop material (or other suitable pouch attachment means) located on pouch attachment point 110 is disposed upon the corresponding material 122 on article of clothing 112. Notably, the portion 128 of pouch 102 that has non-irritating layer of material 126 (described above) is facing out from inner surface 124, so as to be in contact with the skin of user 114 when article of clothing 112 is put on. It is also observed that, in the implementation in FIG. 6, pouch attachment point 110 is disposed on the surface of pouch 102 opposite portion 128, thereby ensuring that layer of material 126 is facing towards user 114 so as to provide maximum comfort.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A catheter bag support sleeve, comprising:
a pouch sized to receive a catheter bag and allow for normal operation of the catheter bag, and the pouch being comprised of a flexible material, the pouch further comprising:
a top end opposite a bottom end, the top end being vertically elevated above the bottom end,
one or more bag attachment points for securing the catheter bag within the pouch,
an opening on a front side of the bag to allow the catheter bag to be drained with a drain valve without removal from the pouch, wherein the opening suspends the drain valve above the bottom end of the pouch, and
one or more pouch attachment points disposed exclusively at the top end of the pouch for removably securing the pouch to an article of clothing configured to be worn by a user, wherein the pouch hangs freely from the article of clothing exclusively by the pouch attachment point.

2. The catheter bag support sleeve of claim 1, wherein each of the one or more bag attachment points for securing the catheter bag within the pouch further comprise a button sized to fit through a receiving slit in the catheter bag.

3. The catheter bag support sleeve of claim 1, wherein the one or more pouch attachment points for removably securing the pouch to an article of clothing configured to be worn by the user further comprises one or more areas of hook or loop material, which attach to corresponding loop or hook material on the article of clothing.

4. The catheter bag support sleeve of claim 3, wherein the corresponding loop or hook material on the article of clothing is located on an inner surface of the article of clothing, configured to allow the user to removably secure the pouch inside the article of clothing.

5. The catheter bag support sleeve of claim 1, wherein the pouch is constructed of a soft material.

6. The catheter bag support sleeve of claim 1, further comprising a layer of soft material attached to a portion of the pouch that is configured to be in contact with the user.

7. The catheter bag support sleeve of claim 5, wherein the soft material attached to a portion of the pouch is constructed of cotton, flannel, satin, or microfiber.

8. The catheter bag support sleeve of claim 1, wherein the pouch is substantially tubular in shape, and has two ends, with each end capable of being sealed closed.

9. The catheter bag support sleeve of claim 1, wherein the pouch is comprised of fabric.

10. A catheter bag support system, comprising:
   a catheter bag;
   a flexible tubular sleeve with a diameter sized to allow insertion and normal operation of the catheter bag;
   one or more bag fasteners for removably securing the catheter bag within the flexible tubular sleeve; and
   an opening on a front side of the sleeve to allow the catheter bag to be drained with a drain valve without removal from the sleeve, wherein the opening is configured to suspend the drain valve above a bottom end of the sleeve; and
   one or more pouch fasteners for removably securing the flexible tubular sleeve to a garment configured to be worn by a user with the catheter bag secured within the flexible tubular sleeve, wherein the pouch hangs freely from the garment by the one or more pouch fasteners.

11. The catheter bag support system of claim 10, wherein the garment being worn by the user further comprises one or more attachment points that correspond to the one or more pouch fasteners for removably securing the flexible tubular sleeve, the attachment points positioned on the garment so as to allow the flexible tubular sleeve to be removably secured inside the garment.

12. The catheter bag support system of claim 10, wherein the flexible tubular sleeve is configured to be affixed shut at one or both ends.

13. The catheter bag support system of claim 12, wherein the flexible tubular sleeve is at least partially constructed from soft material.

14. The catheter bag support system of claim 13, wherein the one or more pouch fasteners for removably securing the flexible tubular sleeve to a garment configured to be worn by a user comprise either hook or loop material, and the one or more attachment points that correspond to the one or more fasteners for removably securing the flexible tubular sleeve comprise corresponding complementary hook or loop material.

15. A catheter bag support sleeve, comprising:
   a pouch that is substantially tubular in shape and sized so as to receive a catheter bag within the pouch without affecting the normal operation of the catheter bag;
   a means for removably securing the catheter bag within the pouch;
   a means for removably securing the pouch to the inside surface of a garment configured to be worn by a user; and
   at least one opening on a front side of the pouch to allow the catheter bag to be drained with a drain valve without removing the catheter bag from the pouch, wherein the opening suspends the drain valve above a bottom end of the pouch, and
   one or more pouch attachment points disposed exclusively at a top end of the pouch for removably securing the pouch to the garment configured to be worn by a user, where the pouch hangs freely from the garment at the top end of the pouch.

16. The catheter bag support sleeve of claim 15, wherein the pouch is at least partially constructed from a soft material.

* * * * *